US00PP32406P2

(12) United States Plant Patent
Lommerse et al.

(10) Patent No.: US PP32,406 P2
(45) Date of Patent: Oct. 27, 2020

(54) ***SANGUISORBA* PLANT NAMED 'JAM SESSION'**

(50) Latin Name: *Sanguisorba officinalis*
Varietal Denomination: Jam Session

(71) Applicants: Gerardus Adrianus Petronella Lommerse, Noordwijkerhout (NL); Hendrikus Petrus Lommerse, Lisse (NL)

(72) Inventors: Gerardus Adrianus Petronella Lommerse, Noordwijkerhout (NL); Hendrikus Petrus Lommerse, Lisse (NL)

(73) Assignee: FUTURE PLANTS LICENTIE B.V., Lisserbroek (NL)

( * ) Notice: Subject to any disclaimer, the term of this patent is extended or adjusted under 35 U.S.C. 154(b) by 0 days.

(21) Appl. No.: 16/602,487

(22) Filed: Oct. 17, 2019

(51) Int. Cl.
*A01H 6/74* (2018.01)
*A01H 5/02* (2018.01)

(52) U.S. Cl.
USPC ..... Plt./263.1

(58) Field of Classification Search
USPC ..... Plt./263.1
CPC ..... A01H 5/02; A01H 6/74
See application file for complete search history.

(56) References Cited

PUBLICATIONS

PLUTO Plant Variety Database Apr. 29, 2020.*

* cited by examiner

*Primary Examiner* — Annette H Para
(74) *Attorney, Agent, or Firm* — C. A. Whealy

(57) ABSTRACT

A new and distinct cultivar of *Sanguisorba* plant named 'Jam Session', characterized by its compact plant habit with upright flowering stems; moderately vigorous growth habit; dark green-colored leaves; numerous white-colored flowers on dense inflorescences; and good garden performance.

2 Drawing Sheets

Figure 1:
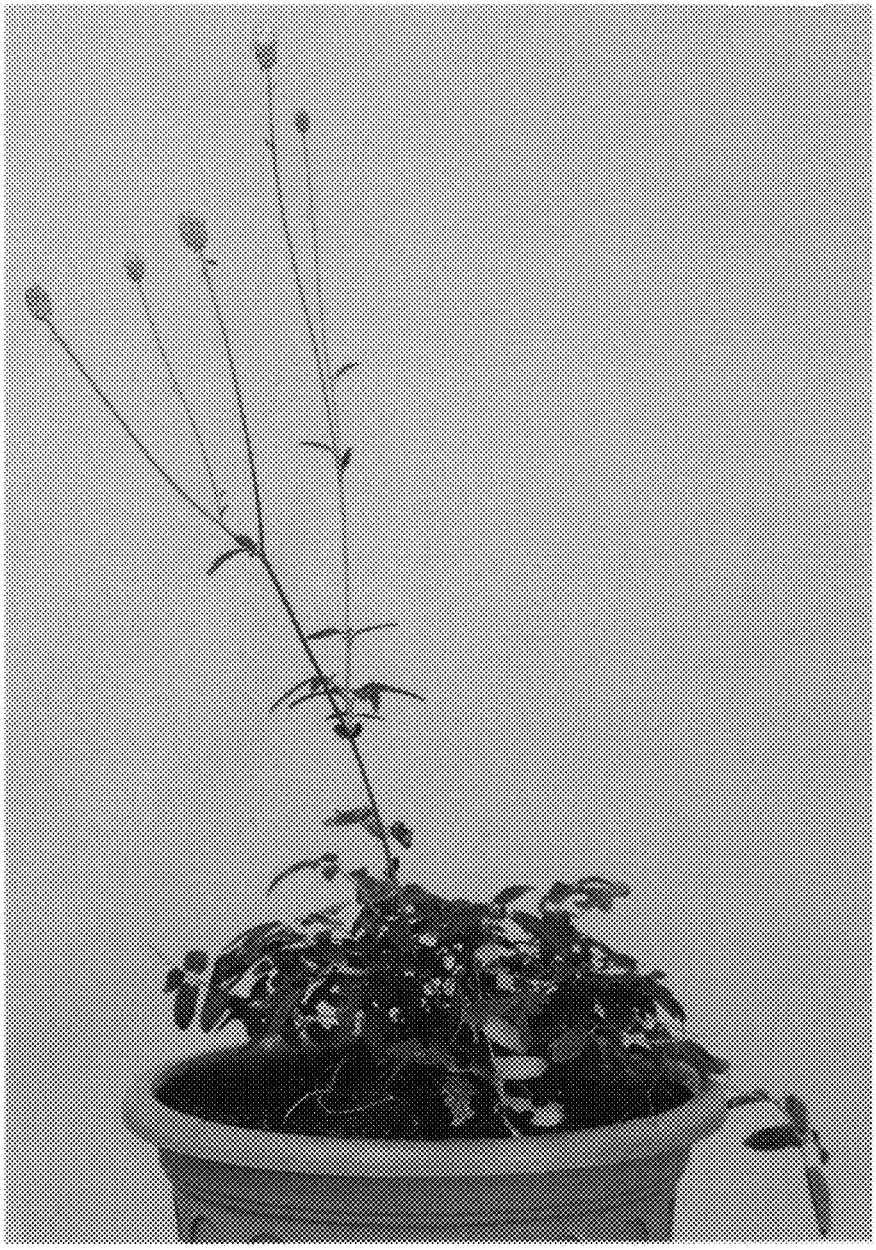
Figure 2:
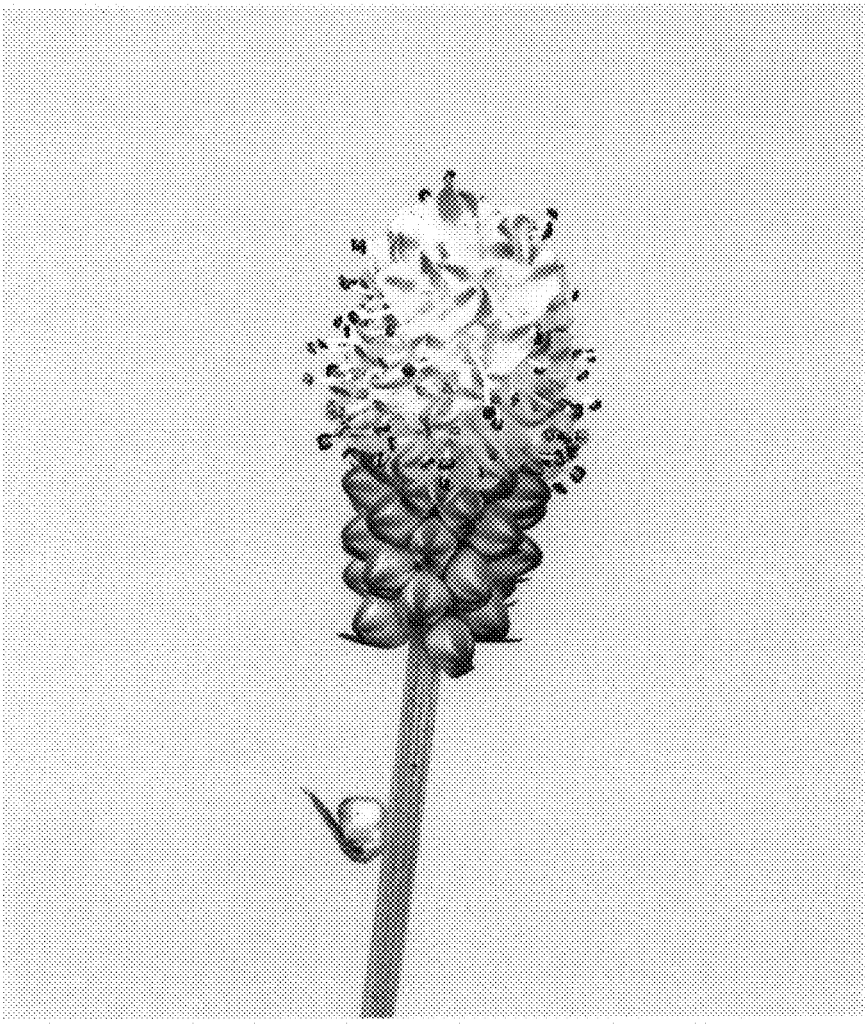

Botanical designation: *Sanguisorba officinalis*.
Cultivar denomination: 'JAM SESSION'.

BACKGROUND OF THE INVENTION

The present invention relates to a new and distinct cultivar of *Sanguisorba* plant, botanically known as *Sanguisorba officinalis* and hereinafter referred to by the name 'Jam Session'.

The new *Sanguisorba* plant originated from an open-pollination during the summer of 2015 in Lisserbroek, The Netherlands, of *Sanguisorba officinalis* 'Red Thunder', not patented, as the female, or seed, parent with an unknown selection of *Sanguisorba officinalis* as the male, or pollen, parent. The new *Sanguisorba* plant was discovered and selected by the Inventors as a single plant from within the progeny of the stated open-pollination in a controlled environment in Lisserbroek, The Netherlands in August, 2016.

Asexual reproduction of the new *Sanguisorba* plant by divisions in a controlled environment in Lisserbroek, The Netherlands since February, 2017 has shown that the unique features of this new *Sanguisorba* plant are stable and reproduced true to type in successive generations.

SUMMARY OF THE INVENTION

Plants of the new *Sanguisorba* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Jam Session'. These characteristics in combination distinguish 'Jam Session' as a new and distinct *Sanguisorba* plant:

1. Compact plant habit with upright flowering stems.
2. Moderately vigorous growth habit.
3. Dark green-colored leaves.
4. Numerous white-colored flowers on dense inflorescences.
5. Good garden performance.

Plants of the new *Sanguisorba* differ primarily from plants of the female parent, 'Red Thunder', in plant habit as plants of the new *Sanguisorba* are more compact than and shorter than plants of 'Red Thunder'. In addition, plants of the new *Sanguisorba* have white-colored flowers whereas plants of 'Red Thunder' have dark pinkish red-colored flowers.

Plants of the new *Sanguisorba* can be compared to plants of *Sanguisorba officinalis* 'Tanna', not patented. Plants of the new *Sanguisorba* differ primarily from plants of 'Tanna' in plant habit as plants of the new *Sanguisorba* are more taller than plants of 'Tanna'. In addition, plants of the new *Sanguisorba* have white-colored flowers whereas plants of 'Tanna' have dark pinkish red-colored flowers.

Plants of the new *Sanguisorba* can also be compared to plants of *Sanguisorba officinalis* 'Proud Mary', not patented. Plants of the new *Sanguisorba* differ primarily from plants of 'Proud Mary' in leaf color as plants of the new *Sanguisorba* have dark green-colored leaves whereas plants of 'Proud Mary' have bluish green-colored leaves. In addition, plants of the new *Sanguisorba* have white-colored flowers whereas plants of 'Proud Mary' have pinkish red-colored flowers.

BRIEF DESCRIPTION OF THE PHOTOGRAPHS

The accompanying colored photographs illustrate the overall appearance of the new *Sanguisorba* plant showing the colors as true as it is reasonably possible to obtain in colored reproductions of this type. Colors in the photographs may differ slightly from the color values cited in the detailed botanical description which accurately describe the colors of the new *Sanguisorba* plant.

The photograph on the first sheet is a side perspective view of typical flowering plant of 'Jam Session' grown in a container.

The photograph on the second sheet is a close-up view of a typical inflorescence of 'Jam Session'.

DETAILED BOTANICAL DESCRIPTION

The aforementioned photographs and following observations, measurements and values describe plants grown during the autumn in 25-cm containers in an outdoor nursery in Lisserbroek, The Netherlands and under cultural practices typical of commercial *Sanguisorba* production. During the production of the plants, day temperatures ranged from 12° C. to 25° C. and night temperatures ranged from 4° C. to 15° C. Plants were one year old when the photographs and description were taken. In the following description, color references are made to The Royal Horticultural Society Colour Chart, 2015 Edition, except where general terms of ordinary dictionary significance are used.

Botanical classification: *Sanguisorba officinalis* 'Jam Session'.

Parentage:

*Female, or seed, parent.*—*Sanguisorba officinalis* 'Red Thunder', not patented.

*Male, or pollen, parent.*—Unknown selection of *Sanguisorba officinalis*, not patented.

Propagation:

*Type.*—By in vitro meristem culture.

*Time to initiate roots, summer.*—About two to three weeks at ambient temperatures about 22° C.

*Time to produce a rooted young plant, summer.*—About eight months at ambient temperatures about 20° C.

*Root description.*—Fine, moderately fibrous; developing roots, close to 158A in color becoming closer to between N199B and N199C with development, actual color of the roots is dependent on substrate composition, water quality, fertilizer type and formulation, substrate temperature and physiological age of roots.

*Rooting habit.*—Freely branching; dense.

Plant description:

*Plant and growth habit.*—Herbaceous perennial typically grown as a garden plant; compact and upright plant habit; moderately vigorous growth habit; moderate growth rate; flattened globular basal rosette with upright flowering stems; basal branching habit with about three primary basal branches developing per plant.

*Plant height, soil level to top of foliar plane.*—About 11.7 cm.

*Plant height, soil level to top of floral plane.*—About 48.3 cm.

*Plant width (spread).*—About 28.3 cm.

*Basal branches.*—Length: About 28.2 cm. Diameter: About 2 mm. Internode length: About 6.5 cm. Strength: Moderately strong. Aspect: Upright to slightly outwardly. Texture and luster: Smooth, glabrous; moderately glossy. Color, developing: Close to 145A. Color, developed: Close to 144A to 144B.

Leaf description:

*Arrangement.*—Alternate, compound; basal and cauline leaves.

*Basal leaves.*—Number of leaflets per leaf: About eleven, occasionally seven or nine. Leaf length: About 13.5 cm. Leaf width: About 6.7 cm. Leaflet length: About 3.2 cm. Leaflet width: About 1.4 cm to 1.6 cm. Leaf shape: Obovate. Leaflet shape: Oblong Leaflet apex: Abruptly acute. Leaflet base: Hastate, lobes free. Leaflet margin: Crenate. Leaflet texture and luster, upper surface: Smooth, glabrous; slightly glossy. Leaflet texture and luster, lower surface: Smooth, glabrous; matte. Leaflet venation pattern: Pinnate. Color: Developing leaflets, upper surface: Close to between 137B and 143A. Developing leaflets, lower surface: Close to 138B. Fully expanded leaflets, upper surface: Close to N137A; venation, close to 146B to 146C. Fully expanded leaflets, lower surface: Close to between 138A and 147B; venation, close to 146C to 146D. Petioles: Length: About 10.2 cm. Diameter: About 1 mm. Texture and luster, upper and lower surfaces: Smooth, glabrous; moderately glossy. Strength: Strong. Color, upper and lower surfaces: Close to 144A; towards the base, close to 187D.

*Cauline leaves.*—Number of leaflets per leaf: About three, occasionally five. Leaf length: About 4.8 cm. Leaf width: About 5.5 cm. Leaflet length: About 2.7 cm to 3.2 cm. Leaflet width: About 1 cm to 1.2 cm. Leaf shape: Broadly ovate. Leaflet shape: Oblong Leaflet apex: Abruptly acute. Leaflet base: Obtuse. Leaflet margin: Crenate. Leaflet texture and luster, upper surface: Smooth, glabrous; slightly glossy. Leaflet texture and luster, lower surface: Smooth, glabrous; matte. Leaflet venation pattern: Pinnate. Color: Developing leaflets, upper surface: Close to between 137B and 143A. Developing leaflets, lower surface: Close to 138B. Fully expanded leaflets, upper surface: Close to N137A; venation, close to 146B to 146C. Fully expanded leaflets, lower surface: Close to between 138A and 147B; venation, close to 146C to 146D. Petioles: Length: About 1.1 cm. Diameter: About 0.75 mm. Texture and luster, upper and lower surfaces: Smooth, glabrous; moderately glossy. Strength: Strong. Color, upper and lower surfaces: Close to 144A.

*Stipules.*—Quantity and arrangement: Two leafy stipulate at the base of each stem leaf. Length: About 9 mm. Width: About 5 mm. Shape: Broadly falcate. Texture, upper and lower surfaces: Smooth, glabrous. Color, upper surface: Close to N137A. Color, lower surface: Close to between 138A and 147B.

Flower description:

*Flower type, arrangement and habit.*—Single rotate flowers arranged on dense terminal racemes; freely flowering habit with about 50 flowers developing per inflorescence and about 750 flowers developing per plant during the flowering season; flowers face mostly outwardly on the raceme.

*Natural flowering season*.—Plants flower during the summer into the autumn in The Netherlands; plants begin flowering about ten months after planting.

*Flower longevity on the plant*.—Individual flowers last about two weeks on the plant; flowers persistent.

*Fragrance*.—Faint, unpleasant.

*Flower buds*.—Length: About 3 mm. Diameter: About 1.75 mm. Shape: Ovoid. Texture and luster: Smooth, glabrous; matte. Color: Close to N157D; axile stripes, close to 143A.

*Inflorescence height*.—About 2 cm.

*Inflorescence diameter*.—About 1.3 cm.

*Flower diameter*.—About 4.5 mm.

*Flower length*.—About 4.5 mm.

*Flower height*.—About 4 mm.

*Petals*.—Quantity and arrangement: Four in a single whorl. Length: About 3 mm. Width: About 2 mm. Shape: Ovate, reflexed. Apex: Acute. Base: Cuneate. Margin: Entire, not undulate. Texture and luster, upper and lower surfaces: Smooth, glabrous, slightly velvety; matte. Color: When opening, upper surface: Close to NN155C; central band, close to 143B. When opening, lower surface: Close to NN155C; central band, close to 143A to 143B. Fully opened, upper and lower surfaces: Close to NN155C; central band, close to 143B; color does not change with development.

*Sepals*.—Quantity and arrangement: Four in a single whorl; cylindrical calyx. Calyx length: About 1 mm. Calyx diameter: About 1.5 mm. Length: About 1 mm. Width: About 0.5 mm. Shape: Narrowly oblong, fused. Apex: Obtuse. Margin: Entire. Texture and luster, upper and lower surfaces: Smooth, glabrous; matte. Color: When opening, upper and lower surfaces: Close to 155B. Fully opened, upper and lower surfaces: Close to 155B.

*Floral bracts*.—Quantity and arrangement: One at the base of each flower. Length: About 2 mm. Width: About 0.75 mm. Shape: Lanceolate. Apex: Narrowly acute. Base: Cuneate. Margin: Entire. Texture, upper and lower surfaces: Smooth, glabrous. Color, upper and lower surfaces: Close to 143B.

*Peduncles*.—Length: About 15.2 cm. Diameter: About 1.25 mm. Aspect: About 10° from vertical. Strength: Moderately strong. Texture and luster: Smooth, glabrous; moderately glossy. Color: Close to 144A.

*Pedicels*.—Length: About 1 mm. Diameter: About 0.5 mm. Aspect: Erect. Strength: Moderately strong. Texture and luster: Smooth, glabrous; matte. Color: Close to 157A.

*Reproductive organs*.—Stamens: Quantity per flower: Four. Filament length: About 2.5 mm. Filament color: Close to NN155D. Anther shape: Broadly oblong. Anther size: About 0.3 mm by 0.5 mm. Anther color: Close to N77A. Pollen amount: Moderate. Pollen color: Close to 14A. Pistils: Quantity per flower: Ten. Pistil length: About 1.2 mm. Stigma diameter: About 0.75 mm. Stigma shape: Club-shaped. Stigma color: Close to 157D. Style length: About 1 mm. Style color: Close to NN155D. Ovary color: Close to NN155D.

*Seeds and fruits*.—To date, seed and fruit production have not been observed on plants of the new *Sanguisorba*.

Pathogen & pest resistance: Plants of the new *Sanguisorba* have not been observed to be resistant to pathogens and pests common to *Sanguisorba* plants.

Garden performance: Plants of the new *Sanguisorba* have exhibited good tolerance to rain, wind and temperatures ranging from −30° C. to 35° C. and to be suitable for USDA Hardiness Zones 4 to 9.

It is claimed:

1. A new and distinct *Sanguisorba* plant named 'Jam Session' as illustrated and described.

* * * * *